(12) United States Patent
Husain (10) Patent No.: US 8,272,741 B2
(45) Date of Patent: Sep. 25, 2012

(54) CATARACT DETECTION EYE CHART

(76) Inventor: Abbas M Husain, Merchantville, NJ (US)

( * ) Notice: Subject to any disclaimer, the term of this patent is extended or adjusted under 35 U.S.C. 154(b) by 150 days.

(21) Appl. No.: 12/892,927

(22) Filed: Sep. 29, 2010

(65) Prior Publication Data

US 2011/0013142 A1 Jan. 20, 2011

Related U.S. Application Data

(63) Continuation-in-part of application No. 12/683,898, filed on Jan. 7, 2010.

(60) Provisional application No. 61/142,986, filed on Jan. 7, 2009.

(51) Int. Cl.
*A61B 3/02* (2006.01)
*A61B 3/00* (2006.01)

(52) U.S. Cl. ........................................ 351/239; 351/246

(58) Field of Classification Search ........... 351/200–246
See application file for complete search history.

(56) References Cited

U.S. PATENT DOCUMENTS

| | | | | |
|---|---|---|---|---|
| 4,257,690 A * | 3/1981 | Howland | ....................... | 351/239 |
| 5,309,185 A * | 5/1994 | Harper | ........................... | 351/202 |
| 5,371,538 A * | 12/1994 | Widger | ........................ | 348/188 |
| 5,801,809 A * | 9/1998 | Husain | .......................... | 351/239 |

* cited by examiner

*Primary Examiner* — Mohammed Hasan
(74) *Attorney, Agent, or Firm* — Patwrite LLC; Mark David Torche (57) ABSTRACT

An eye chart uses a series of sinusoidal lines spaced at intervals selected to discriminate between normal vision and vision impaired by the presence of a cataract. Groups of sinusoidal lines have progressively different distances between the series with one series representing normal vision with the space between the lines growing progressively further apart to indicate the advancement of the cataract. A user counts the number of lines of the group that is clearly distinct. A user with normal vision will be able to count the number of lines, while a person with cataracts will require the space between the lines to be further apart in order to count depending on the stage of cataract development. A light source may be used to indicate night vision problems. A user can record the progression of the cataracts by tracking any changes over time. Different shapes and letters may be used.

6 Claims, 10 Drawing Sheets

CATARACT DETECTION EYE CHART

CROSS REFERENCE TO RELATED APPLICATIONS

This application is a continuation in part of U.S. patent application Ser. No. 12/683,898, filed Jan. 7, 2010, which in turn claims priority to Provisional Application Ser. No. 61/142,986, filed on Jan. 7, 2009, the complete disclosures of each of which are hereby incorporated by reference.

BACKGROUND OF THE INVENTION

Cataracts account for 48% of world blindness or over 18 million people have some cataract development according to the World Health Organization (WHO). In the United States, 42 percent of people between the ages of 52 to 64 have some cataract development, 60% for those between 65 to 74 and 91% for those between the ages of 75 to 85.

There are many causes of cataracts; long-term ultraviolet exposure, radiation, diabetes, hypertension with the most common cause being age. The most successful treatment for cataracts is surgery to remove the occluded lens. Currently, only a thorough eye examination can detect the early onset of a cataract. There is a need for an easy to use screening detection device that enables an early diagnosis of cataracts.

SUMMARY OF THE INVENTION

An eye chart uses a series of sinusoidal lines spaced at intervals selected to discriminate between normal vision and vision impaired by the presence of a cataract. Groups of sinusoidal lines have progressively different distances between the series with one series representing normal vision with the space between the lines growing progressively further apart to indicate the advancement of the cataract. A user counts the number of lines of the group that is clearly distinct. A user with normal vision will be able to count the number of lines, while a person with cataracts will require the space between the lines to be further apart in order to count depending on the stage of cataract development. A light source may be used to indicate night vision problems. A user can record the progression of the cataracts by tracking any changes over time. Different shapes and letters may be used.

Other features and advantages of the instant invention will become apparent from the following description of the invention which refers to the accompanying drawings.

DETAILED DESCRIPTION OF THE INVENTION

In the following detailed description of the invention, reference is made to the drawings in which reference numerals refer to like elements, and which are intended to show by way of illustration specific embodiments in which the invention may be practiced. It is understood that other embodiments may be utilized and that structural changes may be made without departing from the scope and spirit of the invention.

Figure 1:
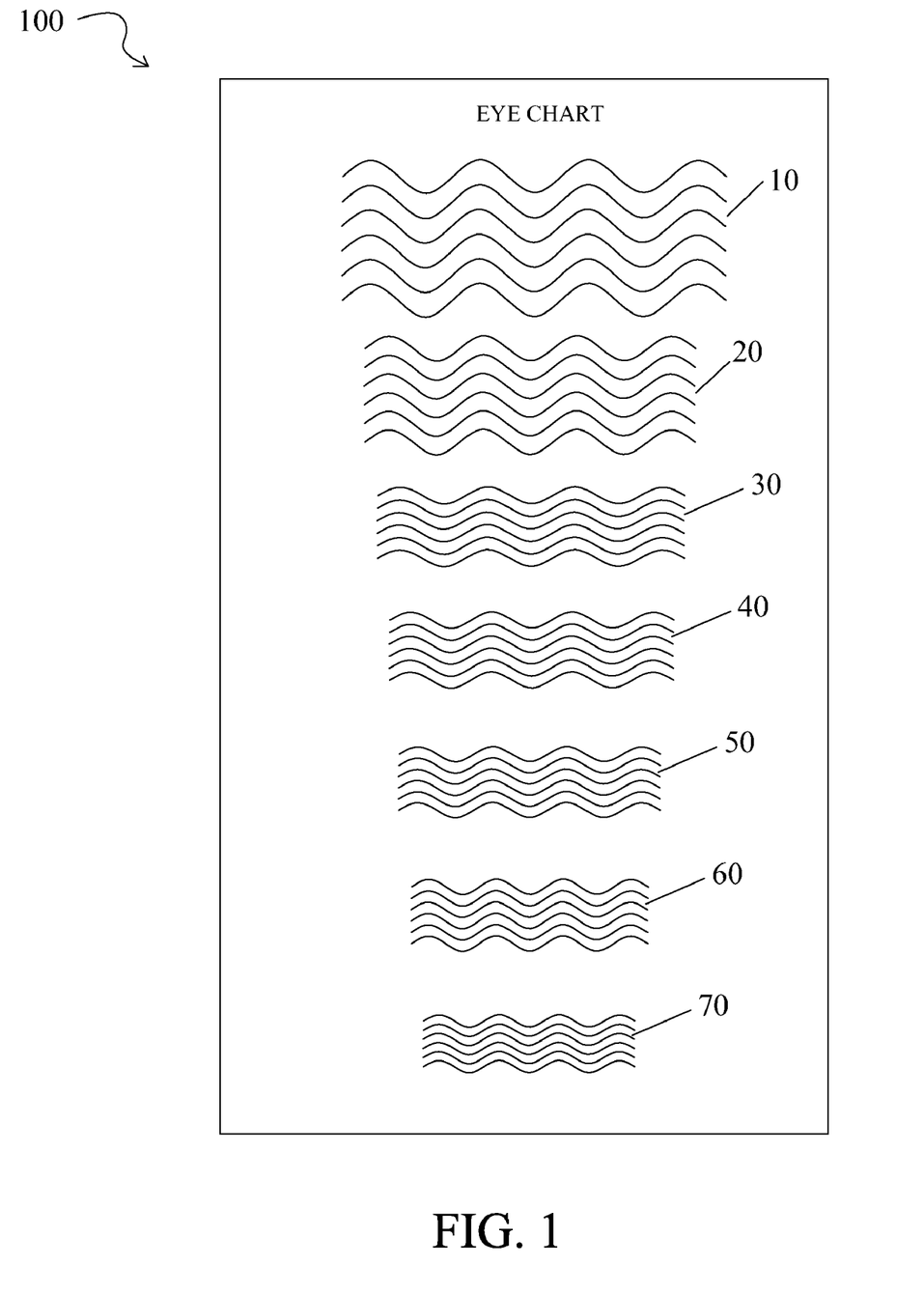
FIG. 1 is a cataract detection chart according to an embodiment of the present invention.

Referring to FIG. 1, a cataract detection eye chart 100 comprises a series of sinusoidal lines. As the user proceeds down the chart 100, the size of the pattern is reduced. Group one lines 10 are spaced 0.3 mm apart and difficulty discriminating at this spacing indicates advanced cataracts. As one proceeds to the group two lines 20, the lines are closer together and are spaced at an interval a user having difficulty discriminating between this spacing indicates progressing cataracts. Likewise group lines three through six; 30, 40, 50 and 60 respectively, reveal progressively lessening cataracts with group seven lines 70 indicating no perceptible cataracts. Of course other spacings may be used and additionally, the spacing may be adjusted for the distance the user will be from the chart 100.

Figure 2:
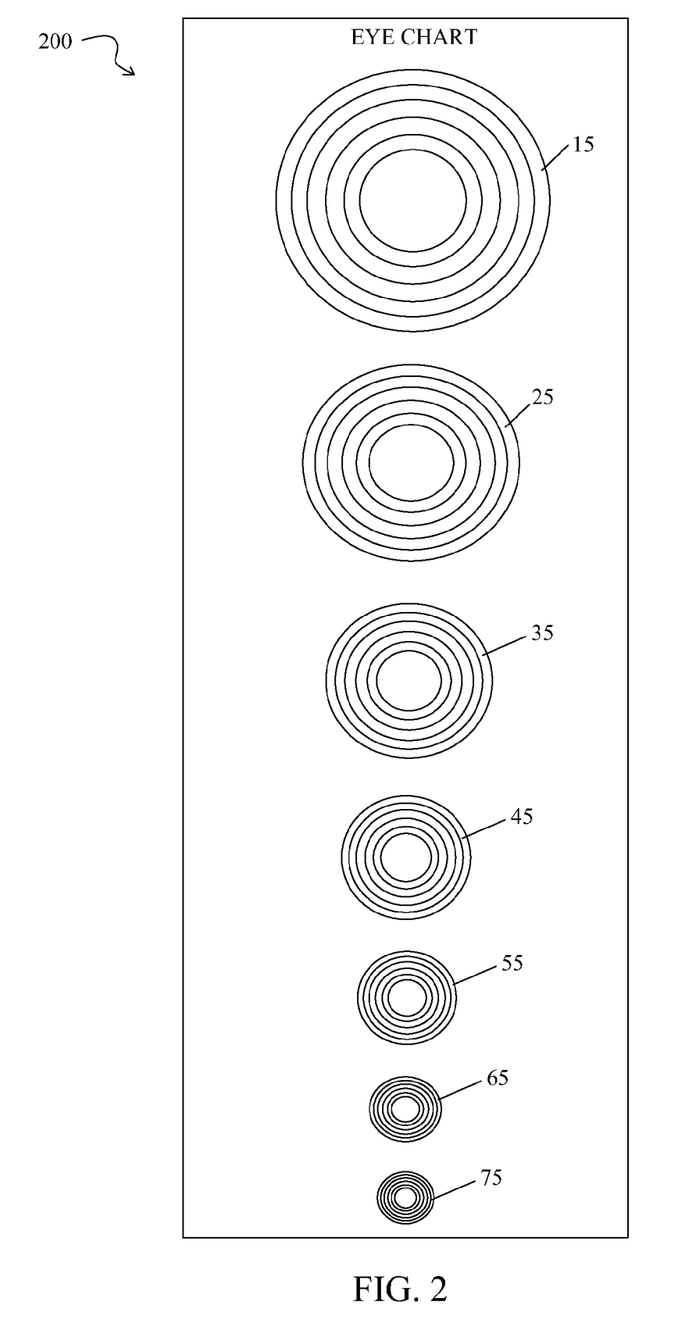
FIG. 2 is a cataract detection chart according to an embodiment of the present invention.

Referring now to FIG. 2, a cataract eye chart 200 is shown having a plurality of circular patterns to indicate the presence of various stages of cataract development. A person only able to discriminate Group one pattern 15 is considered to exhibit an advanced stage of cataract development. Again as in FIG. 1, groups two through six; 25, 35, 45, 55 and 65 respectively, reveal decreasing cataract development with group seven 75 indicating no perceptible cataract development. Again as above, other spacings may be used as well as varying the number of lines used to reduce "expectation error" caused by a user anticipating the number of lines rather than actually reading them.

Of course the number of lines is not critical as long as there are enough lines to present a graphical challenge to discriminate between normal vision and cataract impaired vision. Additionally, the spacing of the lines may be varied.

Figure 3:
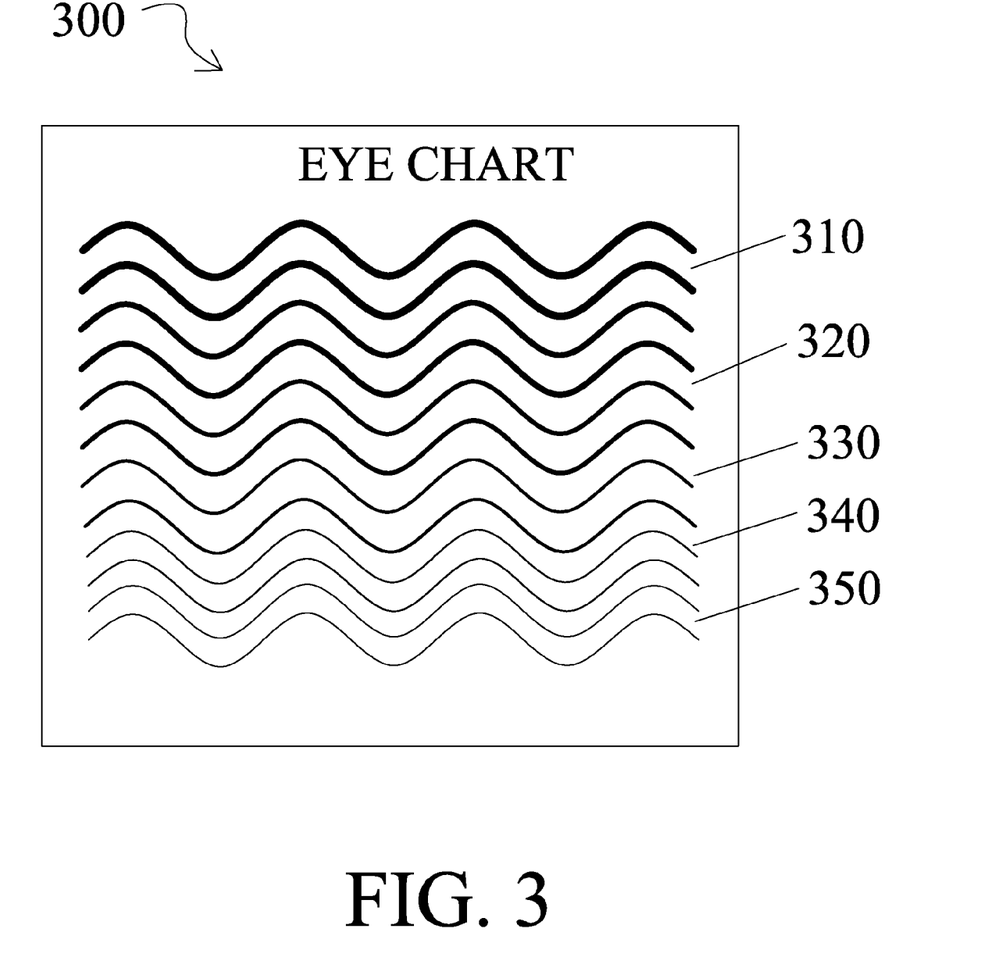
FIG. 3 is a cataract detection chart according to an embodiment of the present invention.

Referring now to FIG. 3, a cataract eye chart 300 is shown having lines grouped together with varying thicknesses. Group one lines 310 have high contrast due to their width and a user only able to discriminate between these lines would be diagnosed as having advanced cataracts. Groups two through four, 320, 330 and 340 respectively, indicate lessening degrees of cataract development with group five 350 indicating unimpaired vision. Again, other contrasting schemes may be utilized such as having as random selection of varying contrasting lines. Additionally, colors could also be used such as having lines in blue or other color to provide an additional level of discrimination. Also, different shades can be used to further refine the optical characteristics such as grey scales where the lines appear from dark to light.

Figure 4:
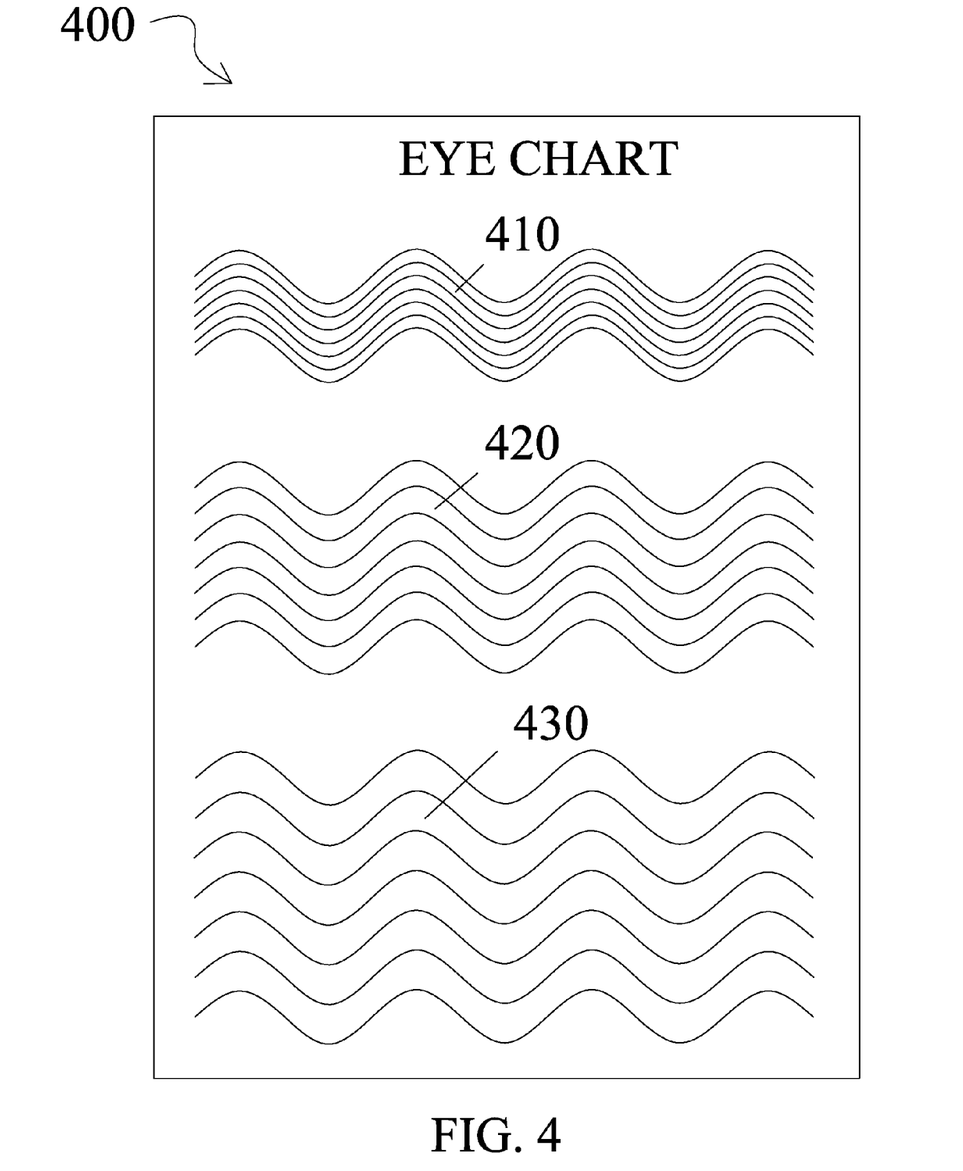
FIG. 4 is a cataract detection chart according to an embodiment of the present invention.

Now referring to FIG. 4, a cataract eye chart 400 is shown with three groups of sinusoidal lines. The first group 410 has 7 lines with small spacings. The second group 420 has 5 lines with intermediate spacings and the third group 430 has six lines with the widest spacings. The number of lines is changed to help avoid an expectation error by a user if the number of lines is the same for all. Of course the number of lines is not critical as long as there are enough lines to present a graphical challenge to discriminate between normal vision and cataract impaired vision.

Figure 5:
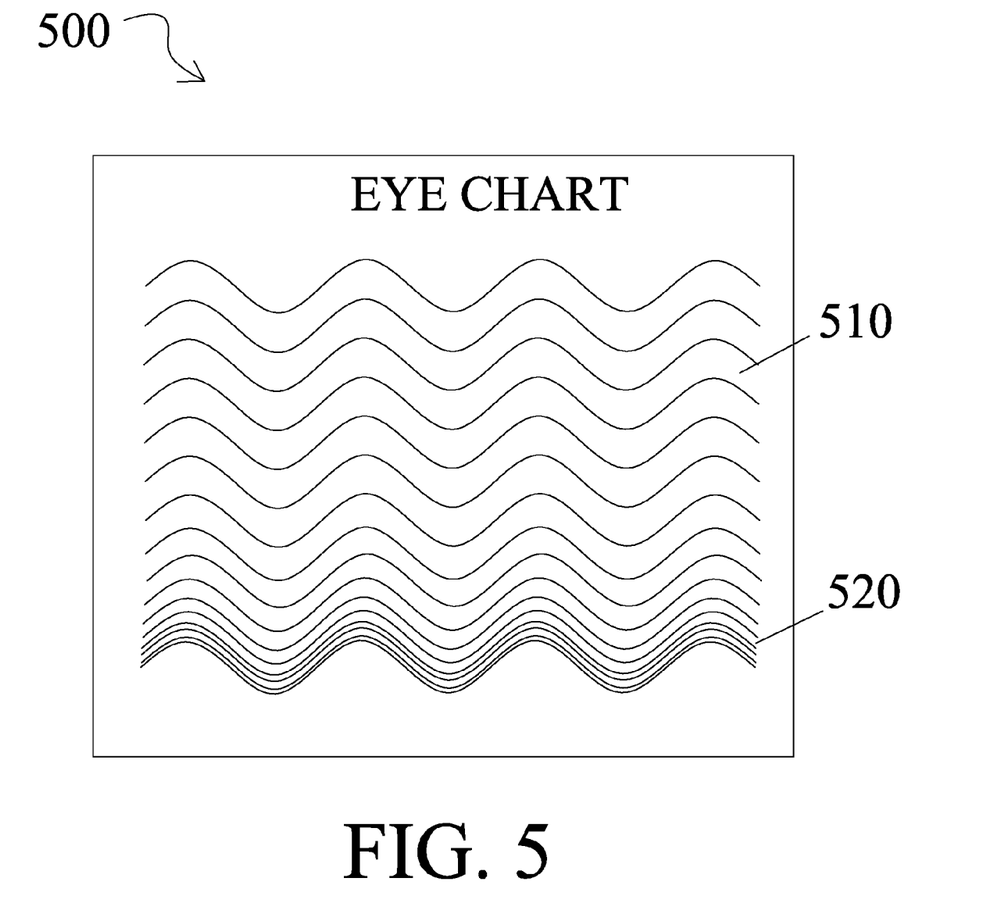
FIG. 5 is a cataract detection chart according to an embodiment of the present invention.

Referring now to FIG. 5, a cataract eye chart 500 is shown having a plurality of sinusoidal lines 510 through 520 that become increasingly closer together. A user is asked to indicate where on chart 500 they are able to discriminate indicating various stages of cataract development. The exact spacing and width of lines may be adjusted depending on the distance from chart 500 the user will be placed.

Figure 6:
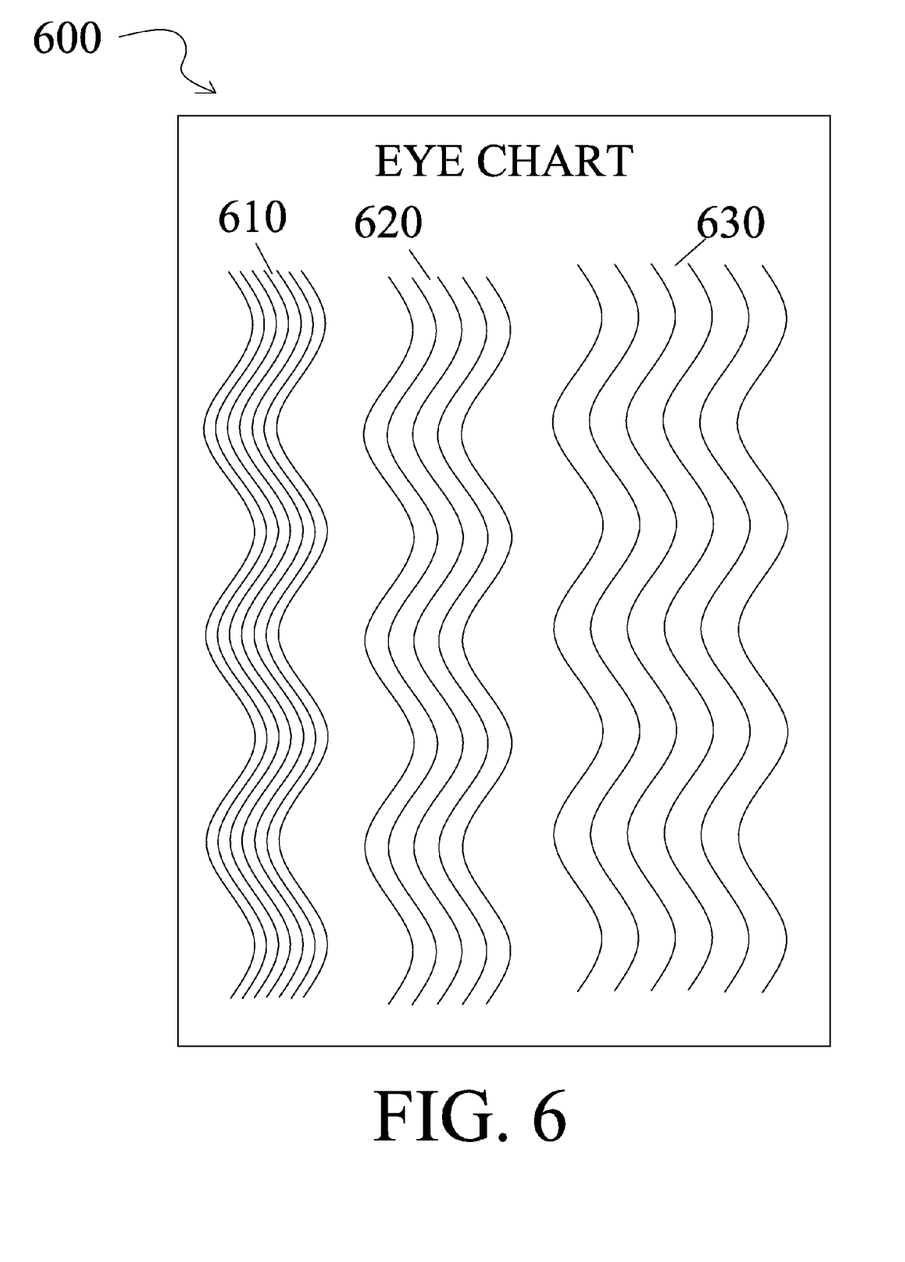
FIG. 6 is a cataract detection chart according to an embodiment of the present invention.

FIG. 6 shows a cataract eye chart 600 having a vertical orientation with three groups of sinusoidal lines. Group one 610 are the closest; second group 620 having an intermediate spacing with the third group 630 being the furthest apart; again as above, discrimination among groups indicate cataract development.

Figure 7:
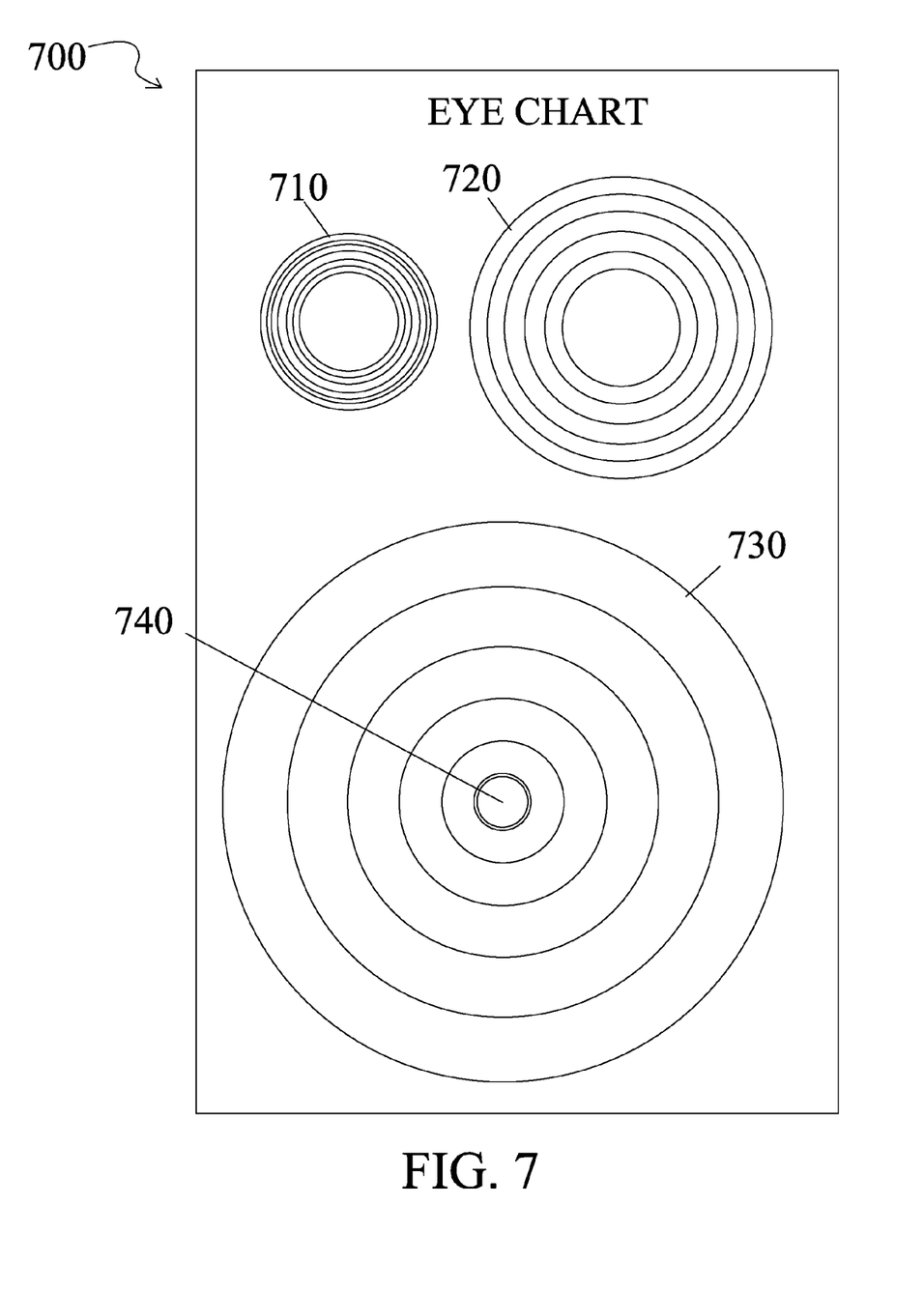
FIG. 7 is a cataract detection chart according to an embodiment of the present invention.

Now referring to FIG. 7, a cataract eye chart 700 is shown having a series of circular patterns to detect and document cataract progression. Group one patterns 710 are the closest together with group two 720 being spaced at an intermediate level and the third group 730 having the widest spacing. Additionally, a light source 740 such as a white light LED or other bright light source may be used to help diagnose cataract development under night driving conditions that may be difficult to detect under normal lighting conditions. Light source 740 may be used with any of the embodiments shown. Of course more or less groups may be used for further levels of discrimination depending on the application.

Figure 8A:
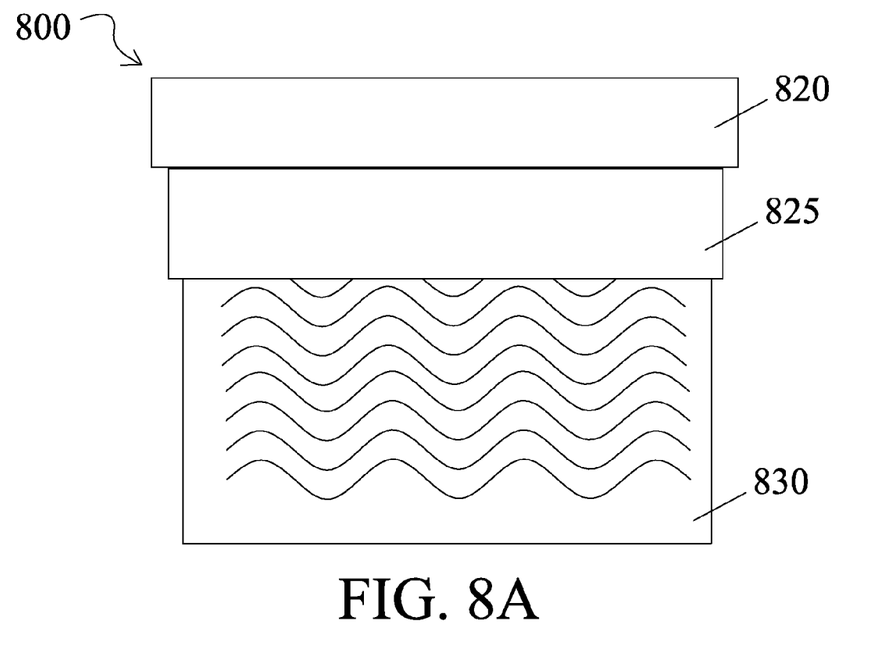
FIG. 8A is a cataract detection chart according to an embodiment of the present invention that utilizes a screen to cover a portion of the chart.
Figure 8B:
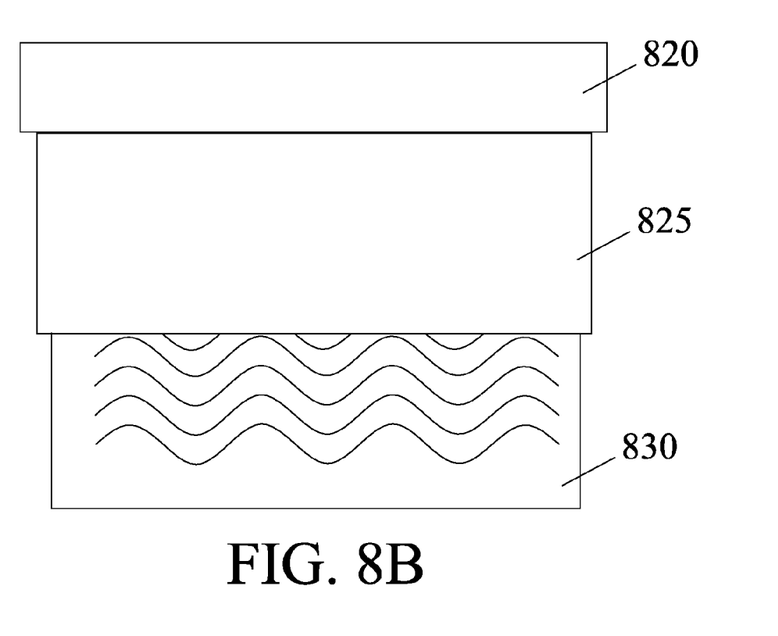
FIG. 8B is a cataract detection chart according to the embodiment of the present invention shown in FIG. 8A with the screen in a second position.
Figure 9A:
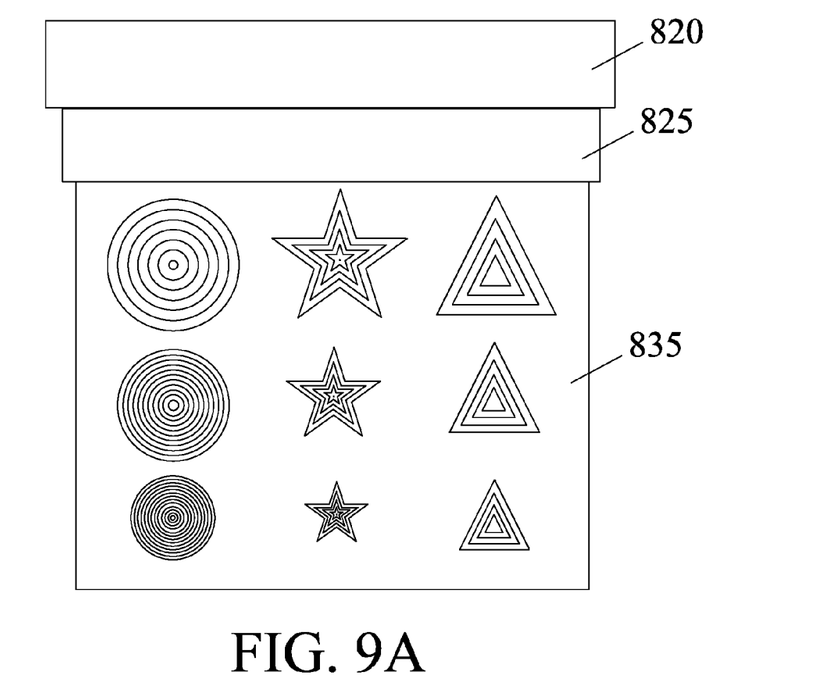
FIG. 9A is a cataract detection chart according to an embodiment of the present invention that utilizes a screen to cover a portion of the chart shown with alternative shapes.
Figure 9B:
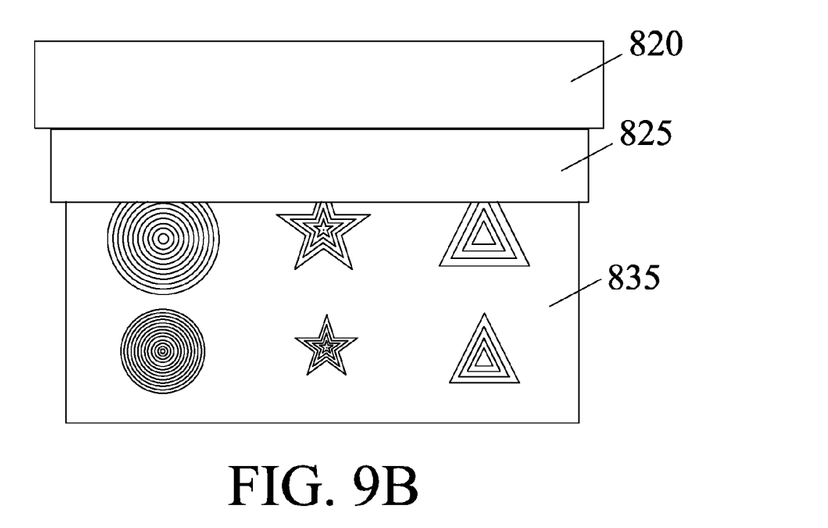
FIG. 9B is a cataract detection chart according to the embodiment of the present invention shown in FIG. 9A with the screen in a second position.
Figure 10:
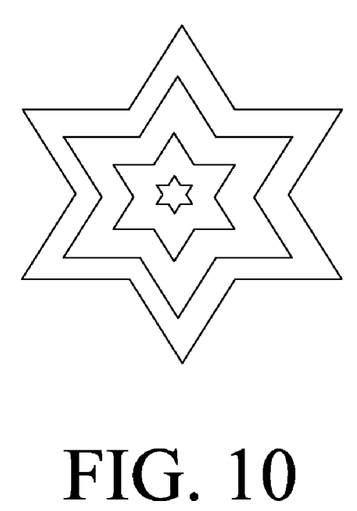
FIG. 10 is an alternative shape for use with the eye chart for cataract detection.
Figure 11:
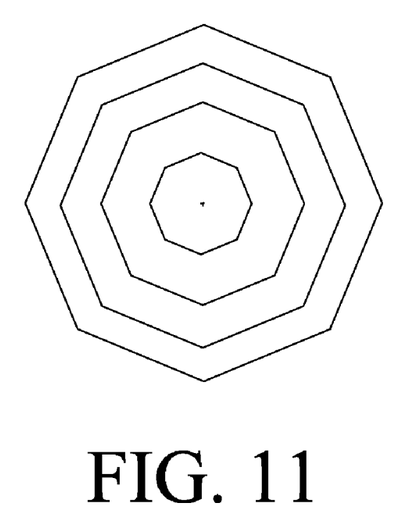
FIG. 11 is an alternative shape for use with the eye chart for cataract detection.
Figure 12:
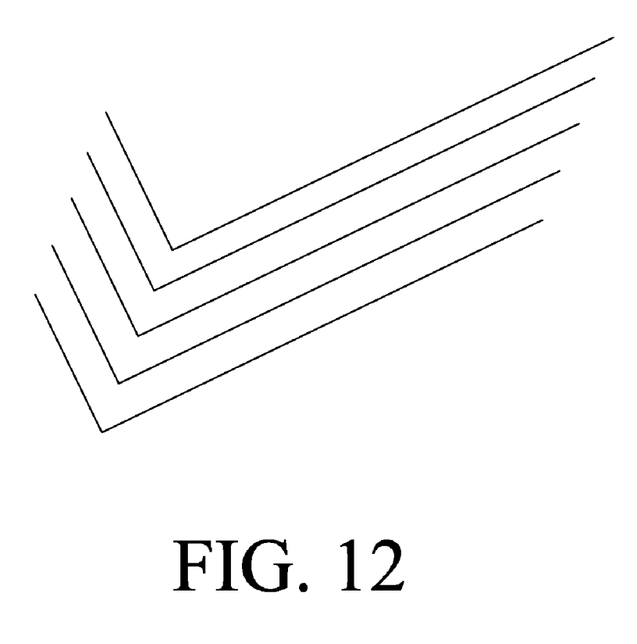
FIG. 12 is an alternative shape for use with the eye chart for cataract detection.

Referring now to FIGS. 8A and 8B, a cataract eye chart 800 is shown with a screen 825 held in a screen holder 820 to cover a portion of an eye chart 830. Screen holder 820 utilizes a retractable mechanism that allows a practitioner to raise and lower the screen as desired while retaining the position as is known in the art. This allows the practitioner to vary the number of lines revealed to reduce expectation error for patients who might remember or pre-count lines to compensate for reduced vision.

If the result of the instant screening reveals a possible problem, the patient may be referred to a specialist for further testing as dictated by standards of care in the health profession. If no problem is indicated, the patient is saved from having to get further testing along with the associated costs. Additionally, the instant method allows a patient to keep track and control the progression of cataracts by recording the results thus allowing the patient and doctor to follow the most advantageous course of treatment.

Referring now to FIGS. 9A, 9B, 10, 11 and 12, cataract detection chart is shown with alternative shapes such as stars, triangles, octagons and checkmarks. This is not meant to be a complete list; rather it is representative of various possible shapes that can be utilized to detect the presence of cataracts in a patient that requires very little expense nor large investments of time. The test is meant to be performed in a doctor's office or other health care facility with minimum investment.

In addition to cataract detection, other eye disorders that result in distortion of vision, may be detected using the instant invention. As an inexpensive and easy non-invasive test, many eye disorders can be identified in an early stage by the routine use of the instant invention before major symptoms become apparent. Some examples of eye disorders that may be detected include glaucoma and astigmatisms as well as others.

Although the instant invention has been described in relation to particular embodiments thereof, many other variations and modifications and other uses will become apparent to those skilled in the art.

What is claimed is:

1. A method of screening a patient for possible eye disorders comprising the steps of:
    obtaining a cataract detection eye chart wherein said cataract detection eye chart comprises;
        a plurality of lines arranged in a pattern adapted to screen said patient for early onset of cataracts;
    positioning a patient at a selected distance from said cataract detection chart;
    instructing said patient to count the number of lines associated with a selected shape on said cataract detection chart;
    recording said patient counts; and
    comparing said patient counts with an actual count wherein any discrepancy will trigger further examination.

2. The method of screening a patient for possible eye disorders according to claim 1 further comprising the step of recording a patient's identification to create a baseline for future evaluations.

3. The method of screening a patient for possible eye disorders using an eye chart according to claim 1 wherein said plurality of lines are produced in a selected color shade.

4. The method of screening a patient for possible eye disorders using an eye chart according to claim 1 wherein said possible eye disorder is cataracts.

5. The method of screening a patient for possible eye disorders using an eye chart according to claim 1 wherein said possible eye disorder is glaucoma.

6. The method of screening a patient for possible eye disorders using an eye chart according to claim 1 wherein said possible eye disorder is astigmatism.

* * * * *